United States Patent [19]

Richmond

[11] 4,059,101

[45] Nov. 22, 1977

[54] THERAPEUTIC DEVICE FOR MASSAGING GINGIVAL TISSUE

[76] Inventor: Martin Richmond, 2505 S. Ocean Blvd., Palm Beach, Fla. 33480

[21] Appl. No.: 669,317

[22] Filed: Mar. 22, 1976

[51] Int. Cl.² .............................................. A61H 7/00
[52] U.S. Cl. .................................. 128/62 A; 32/14 B
[58] Field of Search .... 32/58, 40 R, 14 B; 128/62 A, 128/136

[56] References Cited

U.S. PATENT DOCUMENTS 3,211,149  10/1965  Fono ................................ 128/62 A
3,335,718  8/1967  Sexton ............................. 32/14 B Primary Examiner—Robert Peshock
Attorney, Agent, or Firm—Howard I. Schuldenfrei

[57] ABSTRACT

A mass producible therapeutic device for massaging gingival tissue is disclosed. In the body of the device, oppositely oriented arcuate channels are formed comprising respective recesses generally suited to the conformation of the teeth and adjacent structures. The channels are generally defined by respective pairs of substantially parallel thickened longitudinally extending sidewalls connected through a common interior lateral extension. The body of the device is interiorly slotted or channeled for carrying a fluid, such as air, and the material thereof is sufficiently impermanently deformable so that as a user reciprocably chews into the arcuate channels the effects of fluid redistribution within the body and the elastic character thereof cause the thickened longitudinal sidewalls of the device to flex inwardly against the crowns of the user's teeth for frictionally removing plaque therefrom.

6 Claims, 9 Drawing Figures

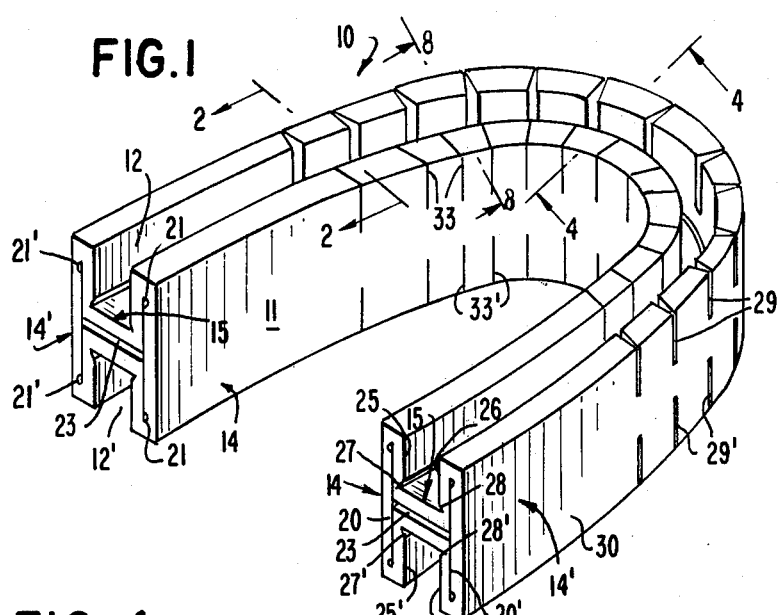
FIG. 1
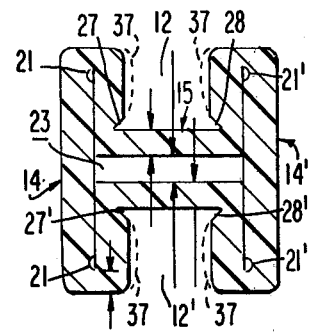
FIG. 2
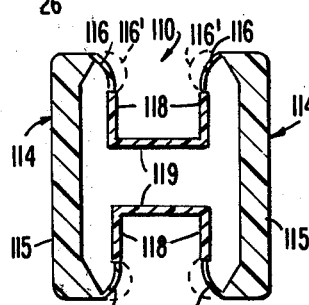
FIG. 3
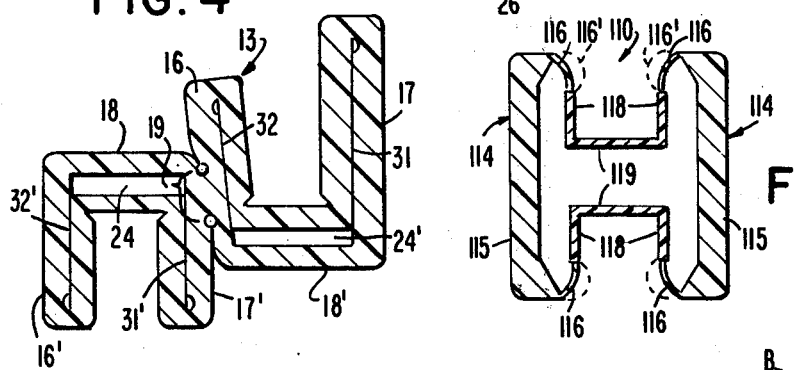
FIG. 4
FIG. 5
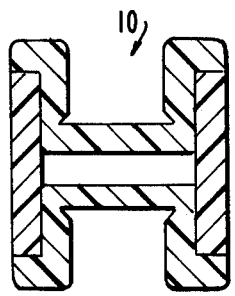
FIG. 6
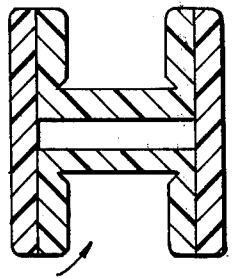
FIG. 7
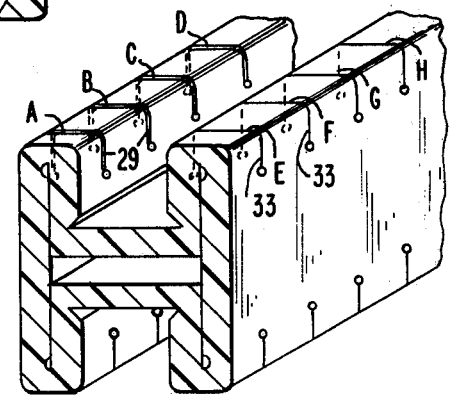
FIG. 8
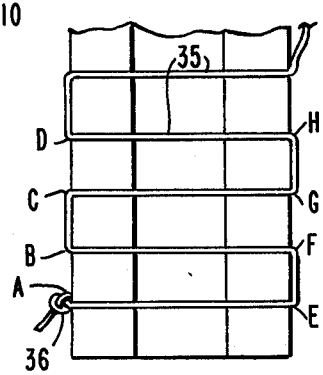
FIG. 9

THERAPEUTIC DEVICE FOR MASSAGING GINGIVAL TISSUE

BACKGROUND OF THE INVENTION

The instant invention relates to a therapeutic device which is removably mountable in a patient's mouth, and when chewed upon is operable for removing plaque deposits therefrom and for massaging and stimulating the gingivae.

While the device may have manifold uses, its novel construction is specifically suited to massaging and stimulating the patient's marginal and interproximal gingivae, thereby strengthening these tissues and rendering them less susceptible to disease. The patient's chewing action actuates the device, whereby the gingivae is reciprocably compressed.

Among its ancillary uses, the device provides means for removing collected plaque from tooth surfaces, for preventing bruxism and concomitant periodontal destruction, and for preventing traumatic damage to the teeth. While the device may be standardized to conventional dental conformations, the standards may be customized to a patient's individual dentition with relative ease.

SUMMARY OF THE INVENTION

Generally speaking, in accordance with the invention, a therapeutic device is disclosed having for its principal utility the massaging of gingival tissue. The device is standarized to various dentition conformations; however, a standard may be customized, if desirable, to an individual patient's dentition and gingivae with an integral complementary biocompatible insert cohesively mounted or cemented in the device.

The device may have either a unitary or composite construction and may be fabricated of resilient materials such as silicone, rubbers, plastics and the like. Whether of unitary or composite construction, the device includes areas of relatively selectively greater elasticity for purposes hereinafter described in detail.

In general, the device comprises a molded body of elastomeric material having arcuate upper and lower channels conforming substantially to the upper and lower jaws of the user, the upper channel being superposed in the molded body relative to the lower channel. The channels are generally defined by respective pairs of substantially parallel thickened longitudinally extending sidewalls connected through a common interior lateral extension. The body of the device is interiorly slotted or channeled for carrying a fluid, such as air, and the material thereof is sufficiently impermanently deformable so that as a user reciprocably chews into the arcuate channels the effects of fluid redistribution within the body of the device and the elastic character thereof cause the thickened longitudinal sidewalls of the device to flex inwardly against the crowns of the user's teeth for frictionally removing plaque therefrom.

According to one embodiment of the device, coplanar free ends of the pairs of thickened sidewalls in the body of the device are determined so as to abut into and compress marginal and interproximal gingivae surrounding the teeth as the user chews into the device, and as the user reciprocably chews into the device the gingival tissue surrounding the user's teeth is massaged and stimulated. According to another embodiment of the device, the interior edges of the free ends are beaded and flex inwardly as the device is chewed upon so as to abut into and massage the gingivae. According to yet another embodiment of the device, the anterior wall of the free end of the device is thinned and impermanently expands, deforming inwardly against the gingivae as the device is chewed on. This gingivae massage and stimulation is accomplished without any degree of manual dexterity and without harming the gingival tissue, although the device is not prescription molded to the exact form of the user's dentition and gingivae.

Accordingly, it is a principal object of the invention to provide a therapeutic device for massaging and stimulating the marginal and interproximal gingivae for thereby strengthening these tissues and rendering them less susceptible to disease.

Another object of this invention is to provide a mass producible therapeutic device for massaging and stimulating gingival tissue, without harming these tissues.

Still another object of this invention is to provide a therapeutic device which acts as an adjuvant for removing plaque from clinical crowns of teeth, while massaging and stimulating gingival tissue.

Yet another object of this invention is to provide a mouthguard type device wearable by the user while asleep for preventing bruxism and concomitant periodontal destruction from occlusal trauma, temporo-mandibular joint disturbances, and myo-fascial pain syndrome from the overstresses of occlusion.

Still another object of this invention is to provide a device having therapuetic uses which may also be used as a mouthguard in contact sports for thereby avoiding traumatic damage to the teeth.

Still other objects and advantages of the invention will, in part, be obvious and will, in part, be apparent from the specification.

The invention accordingly comprises the features of construction, combinations of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of an embodiment of the therapeutic device constructed in accordance with the instant invention;

FIG. 2 is a sectional view of the embodiment seen in FIG. 1, taken along line 2—2 thereof;

FIG. 3 is a sectional view of the embodiment of the therapeutic device seen in FIG. 1 practiced in accordance with the instant invention;

FIG. 4 is a sectional view of the embodiment seen in FIG. 1, taken along line 4—4 thereof;

FIG. 5 is a sectional view of yet another embodiment of the device constructed in accordance with the instant invention;

FIG. 6 is a sectional view of the embodiment seen in FIG. 1, showing a detail of a composite construction for the device;

FIG. 7 is also a sectional view of the embodiment seen in FIG. 1, showing a detail of another composite construction for the device;

FIG. 8 is an isometric detail of the embodiment seen in FIG. 1, the embodiment including means for stringing a floss bridge through the device for cleaning between adjacent surfaces of teeth while massaging the gingivae; and FIG. 9 is a plan view of the embodiment seen in FIG. 8.

DETAILED DESCRIPTION OF THE INVENTION

Referring generally to the drawing, like numbers are used to designate like parts in the various views. Referring particularly to the embodiment seen in FIGS. 1-4, the therapeutic gingival massaging device, generally designated by the numeral 10, comprises a body member 11 of substantially H-shaped cross-section as seen in FIG. 2 which is arcuately longitudinally conformed, as seen in FIG. 1, to fit the mouth from the front to rear, overfit both upper and lower teeth and abut against adjacent gingival tissue. In the sectional view seen in FIG. 4, upper and lower sections of body member 11 are offset to accommodate the overbite of the user's maxillary and mandibular anterior teeth. The action mechanism of the device for massaging and stimulating gingival tissue is best seen in FIG. 3. As seen in these figures, the device has a unitary intergral construction, the body member 11 thereof being formed of silicone, rubber, plastic or other resilient material.

Formed in body member 11 is an upper channel 12 and a lower channel 12', both channels longitudinally extending through body member 11 of the device to respectively accommodate teeth in the upper and lower jaws, the channels being generally superposed, except for an anterior offset portion thereof, generally denoted by numeral 13, designed to accommodate the overbite of the anterior teeth. Channels 12 and 12' are generally defined in body member 11 by thickened longitudinally extending webs 14 and 14' issuing upwardly and downwardly from generally opposite ends of transversely extending bridging web 15.

As best seen in FIG. 4, the structural definition of channels 12 and 12' is designed to accommodate the natural overlapping arrangement of the anterior teeth. Web 14 comprises respectively offset upwardly extending section 16 and downwardly extending section 16', and concomitantly, web 14' comprises respectively offset sections 17 and 17'. Bridging web 15 comprises mirror image sections 18 and 18' connected through an integral joint 19. Sections 16' and 17' of respective webs 14 and 14' issue downwardly from section 18 of bridging web 15, whereas sections 16 and 17 of respective webs 14 and 14' issue upwardly from section 18' thereof.

By referring to FIGS. 1 and 2, it will be seen that webs 14 and 14' each carry a respective interiorly located substantially linear slit 20 and 20' extending continuously therethrough. Opposed ends of slits 20 and 20' terminate in respective pairs of graduated notches 21 and 21'. In the rearward or posterior portions of the device, slits 20 and 20' are each respectively vertically continuous in their webs. However, in the anterior portion of the device as best seen in FIG. 4, the slits are discretely divided into vertical sections 31, 31' and 32, 32' corresponding to the offset construction of webs 14 and 14'.

Referring again to FIGS. 1 and 2, it will be seen that bridging web 15 is interiorly slotted. Rearwardly in the device, bridging web 15 carries a slot 23 laterally extending between slits 20, 20' and communicating therewith. As slot 23 extends anteriorly through web 15 from posterior portions of the device, it bifurcates into companion channels 24 and 24' corresponding to the bridging web construction of sections 18 and 18' in the anterior 13 of the device, as seen in FIG. 4, these companion channels similarly respectively laterally extending between pairs of slits 31', 32' and 31, 32 and communicating correspondingly therewith.

As seen in FIGS. 1 and 2, web 14 has a pair of interior surfaces 25 and 25' issuing incipiently oppositely from web 15 through respective chamfers 27 and 27'. Similarly, web 14' has a pair of interior surfaces 26 and 26' issuing from web 15 in like manner through chamfers 28 and 28'. The emphases of chamfers 27, 27' and 28, 28' may decrease as the anterior portion of the device is approached, until interior surfaces of respective web sections 16, 17 and 16', 17' respectively linearly intersect sections 18' and 18 of the bridging web at the anterior of the device.

As seen in FIG. 1, discretely aligned pluralities of slots 29 and 29' are provided in oppositely issuing ends of web 14', the respective pluralities of slots 29 and 29' extending towards bridging web 15. Each of the slots 29 and 29' extends inwardly from interior surface 26 and 26' of web 14' towards exterior surface 30 thereof. Corresponding pluralities of slits 33 and 33' are provided in web 14 of the device.

In practice, device 10 is chewed upon in the manner illustrated in FIG. 2 until it is elastically deformed to the position seen in FIG. 3 wherein ends of webs 14 and 14' are flexed inwardly for compressing the marginal and interproximal gingivae. As the device is repeatedly chewed upon, the gingival tissue is massaged and stimulated and plaque formations on the teeth are loosened. The interior surfaces of webs 14 and 14' may be beaded to increase gingival stimulation.

By narrowing the breadth of the slots 29 and 29', device 10 may be modified to clean its user's teeth with dental floss, as best seen in FIGS. 8 and 9. A length of dental floss 35 is knotted at one end 36 thereof and introduced into a slot A, pulled taut, introduced into a slot E, then a slot F, and a slot B and so on until a lattice work of the type seen in FIG. 9 is formed. As device 10 is chewed upon, the floss lattice cleans interproximal spaces between the teeth, while the gingivae is massaged and stimulated.

When desirable device 10 may be customized to suit a patient's individual dentition, as shown in phantom in FIG. 2. A biocompatible insert 37 may be fastened or bonded by conventional mechanical or chemical means to the device for the purpose of custom fitting the device to the user's gum line.

Device 10 may be fabricated by conventionally known processes, such as blow molding, extrusion, injection and compression molding processes. The molded article may be machined, cut, or ground to standard size, if necessary. As seen in FIGS. 6 and 7, the device 10 may comprise a bonded composite of individually molded sections. The individual sections of these composites may be fabricated of different materials or may be molded by different processes.

Referring now to FIG. 5 another embodiment of the device, 110, may be seen. According to this embodiment webs 114 have thickened outer walls 115, expansible elastically deformable interior end portions 116 connected to resilient interior sidewalls 118, in turn, integrally connected to bridging webs 119. The interior of the device is substantially hollow and adapted to house a fluid, such as air or a non-toxic liquid. As the device is chewed upon, bridging webs 119 are compressed inwardly, and end portions 116 expand outwardly to a position 116', seen in phantom, into the gingivae as fluid redistributes within the device. Upon release of the chewing pressure on the device, it returns to the position seen in FIG. 5 in solid line. As the device is repeatedly chewed upon, the gingivae is massaged and stimulated.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A therapeutic device for, inter alia, massaging gingival tissue comprising a body member having an arcuate longitudinal conformation so as to fit the mouth from front to rear, said body member including first and second longitudinally extending webs, and a transverse web bridging between said first and second longitudinally extending webs, said first and second longitudinally extending webs each respectively issuing upwardly and downwardly from substantially opposite ends of said transverse bridging web, said first and second longitudinally extending webs and said transverse web defining upper and lower generally superposed channels in said body member, said upper and said lower channels respectively accomodating teeth in the upper and lower jaws of a user of said device; said transverse bridging web comprising first and second overlying webs of predetermined thickness, said first and second overlying webs defining therebetween an interiorly located continuous transverse slot, said first and second overlying webs being compressible through the area of said transverse slot for elastically impermanently deforming said first and second longitudinally extending webs inwardly towards the clinical crowns of teeth and into the gingivae of a user of said device; said first and said second longitudinally extending webs each carrying at least one interiorly located substantially linear slit extending continuously therethrough, said at least one slit in each of said webs terminating in at least one graduated notch of predetermined configuration, said first and second longitudinally extending webs being respectively expansible about its at least one slit in opposite correspondence to a compressive force exerted upon said transverse bridging web, and each of said first and second longitudinally extending webs including a corresponding pair of interior surfaces, each pair of said interior surfaces issuing incipiently oppositely from said transverse bridging web through a corresponding pairs of chamfers, said chamfers having a continuous emphasis throughout said device; said first longitudinally extending web having an upper and a lower end, each of said upper and said lower ends having a discretely aligned plurality of slots therein, each of said slots opening outwardly into a corresponding upper and lower channel, and said second longitudinally extending web having an upper and a lower end, each of said upper and lower ends having a discretely aligned plurality of slits therein, each of said slits in said second longitudinally extending web corresponding to a slot in said first longitudinally extending web, said first and second longitudinally extending webs being respectively contractable through the areas of their respective slots and slits as a compressive force is exerted through said transverse bridging web for thereby overfitting the clinical crowns of teeth and abutting the gingivae of a user of said device.

2. The device as claimed in claim 1, including a continuous bead mounted along respective pairs of interior surfaces of said first and second longitudinally extending webs, said bead providing a gingivae stimulus when in contact therewith.

3. The device as claimed in claim 1, wherein bases of respective pluralities of slots and slits, respectively in said first and second longitudinally extending webs have notches therein adapted to releasably receive dental floss therein.

4. The therapeutic device as claimed in claim 1, including a lattice of dental floss mounted through alternately corresponding slots and slits in said respective first and second longitudinally extending webs for cleaning interproximal areas between teeth of a user of said device.

5. The therapeutic device as claimed in claim 1, said body member being fabricated of silicone, plastic or rubber.

6. The therapeutic device as claimed in claim 1, including a custom molded insert mounted in each of said upper and lower channels for thereby customizing said device to the particular dentition of its user.

* * * * *